United States Patent [19]
Parkinson et al.

[11] Patent Number: 5,478,723
[45] Date of Patent: Dec. 26, 1995

[54] METHOD AND APPARATUS FOR DETERMINING THE ROLE OF CYTOCHROME P450 AND RELATED ENZYMES IN THE METABOLISM OF DRUGS AND OTHER CHEMICALS

[76] Inventors: Andrew Parkinson, 7538 Mohawk, Prairie Village, Kans. 66208; Dorn C. Cook, 5914 S. Lakeshore Dr., Tempe, Ariz. 85283

[21] Appl. No.: 127,317

[22] Filed: Sep. 27, 1993

[51] Int. Cl.$^6$ .............................. C12Q 1/00; C12Q 1/26; C12N 9/02; G01N 33/483
[52] U.S. Cl. ................... 435/4; 435/25; 435/189; 435/966; 436/63; 436/64; 530/846
[58] Field of Search ................... 435/6, 4, 189, 435/25, 966, 975, 967; 514/12, 21; 530/846; 424/2, 9; 436/63, 64

[56] References Cited

U.S. PATENT DOCUMENTS 4,066,510  1/1978  Thilly ............................................ 435/6
5,100,779  3/1992  Watkins ...................................... 435/25

OTHER PUBLICATIONS

Schenkman "Cytochrome P450" pp. 503–524, 1993.
Waterman "Methods in Enzymology" vol. 206 pp. 141–190, 1991.
Jerina "Drug Metabolism Concepts" pp. 46–71 & 81–98 1977.
Dybing et al. "In Vitro Metabolism & Activation of Carcinogenic Aromatic Amines by Subcellular Fractions of Human Liver" Cancer Res 39 4206–4211 1979.

*Primary Examiner*—Michael G. Wityshyn
*Assistant Examiner*—Nancy J. Degen
*Attorney, Agent, or Firm*—Tod R. Nissle

[57] ABSTRACT

A method and apparatus for determining the enzyme or enzymes in the human body which metabolize a particular drug. Microsomes are obtained from each of several donors. The microsome for one donor is reacted with a test drug and the quantity of metabolites produced is determined. The microsomes are similarly each reacted with the test drug and the quantity of metabolites produced for each microsome is determined to generate drug metabolism data. The drug metabolism data obtained is compared to reference data which indicates the activity of a select number of major enzymes in each of the donors. The reference data for each enzyme is separately tabulated. The enzyme responsible for the metabolism of the test drug is identified when the metabolism data correlates with the tabulated reference data for that enzyme.

2 Claims, 4 Drawing Sheets

METHOD AND APPARATUS FOR DETERMINING THE ROLE OF CYTOCHROME P450 AND RELATED ENZYMES IN THE METABOLISM OF DRUGS AND OTHER CHEMICALS

This invention relates to a method and apparatus for determining the enzyme or enzymes in the human body which metabolize a particular drug.

In a further respect, the invention relates to a kit for identifying enzymes which metabolize a particular drug.

In still another respect, the invention relates to a method and apparatus for determining the liver enzyme or enzymes which metabolize a drug.

In yet another respect, the invention relates to a method for determining whether a chemical is mutagenic.

The liver contains enzymes that convert various chemical compositions to products, called metabolites, which can be more easily eliminated from the body, usually in the urine or feces. This conversion process, which is also known as chemical metabolism or chemical biotransformation, frequently determines the duration of action of pharmaceuticals or the intensity of the pharmaceutical action, which is why pharmaceuticals must typically be taken several times each day to treat diseases and produce other desirable pharmacological effects.

The many pharmaceutical-metabolizing enzyme systems of the liver include cytochrome P450, carboxylesterases, UDP-glucuronosyltransferases, sulfotransferases, glutathione S-transferases and many others. Each of these enzyme systems is comprised of numerous individual enzymes, each of which is capable of metabolizing a wide variety of pharmaceuticals and other chemical compositions. For example, the cytochrome P450 system in the human liver is comprised of at least ten individual P450 enzymes. Of these various enzyme systems, the P450 enzymes play the most important role in determining the rate of elimination of drugs.

Without cytochrome P450 and related enzymes, the naturally occurring and man-made foreign chemicals to which we are unavoidably exposed would accumulate in the body and overwhelm us. It is important to realize, however, that the biological or toxic effects of some chemicals are due to metabolites generated by cytochrome P450 and/or related enzymes. For example, the pharmacological effects of the anti-histamine, Seldane, are not due to its main ingredient, terfenadine, but are instead due to a metabolite of terfenadine that is generated by cytochrome P450. Similarly, the liver toxicity that can result from taking acetaminophen, the active ingredient in tylenol, is not due to acetaminophen per se, but is due to a toxic metabolite that is generated by cytochrome P450.

Metabolism by cytochrome P450 often represents the rate-limiting step in pharmaceutical elimination. Consequently, factors that lessen the activity of P450 enzymes usually prolong the effects of pharmaceuticals, whereas factors that increase cytochrome P450 activity have the opposite effect.

Changes in pharmaceutical metabolism may have undesirable or toxic consequences. For example, impaired metabolism of a pharmaceutical by factors that decrease cytochrome P450 activity may lead to symptoms of pharmaceutical overdose. In particular, the anti-coagulant warfarin can cause bleeding disorders when administered to individuals with low cytochrome P450 activity. Since the ulcer treatment drug cimetidine depresses P450 activity, warfarin is not administered to patients on cimetidine. Conversely, the accelerated metabolism of a drug due to increased concentrations of cytochrome P450 can also lead to a lessening of therapeutic effect. For example, pharmaceuticals such as phenobarbital and rifampin that increase cytochrome P450 activity lead to an increased rate of metabolism of contraceptive steroids. When the contraceptive steroids are consumed ovulation, and pregnancy, can result.

As noted, the liver converts many chemicals other than pharmaceuticals to metabolites that can be more readily eliminated from the body. Cytochrome P450 and related enzymes facilitate the elimination of endobiotics and of numerous foreign chemicals called xenobiotics. Xenobiotics include environmental pollutants, pesticides, industrial chemicals, household products, cosmetics and non-nutrients in food. Non-nutrients in food include plant alkaloids, flavorings, and chemicals that form during spoilage or cooking. Because of the broad range of chemicals metabolized by cytochrome P450 and other enzymes, the terms xenobiotic-metabolizing enzymes and xenobiotic biotransforming enzymes can be used to describe cytochrome P450 and other related enzymes. Endobiotics are chemicals made in the body, such as steroid hormones, elcosanoids, and fat-soluble vitamins. In view of the wide range of chemicals which can be metabolized by cytochrome P450 and/or related enzymes or other enzymes, the term drug is used herein to means any chemical, endogenous or foreign, that is metabolized by cytochrome P450 and/or related enzymes or other bodily enzymes.

The need to identify which enzyme or enzymes are responsible for metabolizing a drug is long standing. For example, information on which particular P450 enzyme is responsible for metabolizing a drug can be used to explain and predict a variety of adverse drug reactions and reactions which occur when two or more drugs are simultaneously ingested by an individuals. When administered with ketoconazole or erythromycin, the anti-histamine Seldane (active ingredient, terfenadine) causes Torsades de Points, which in some individuals leads to ventricular arrhythmias and heart failure. This drug—drug interaction can be explained on the basis that terfenadine is extensively metabolized by intestinal and hepatic CYP3A enzymes. When these enzymes are inhibited by ketoconazole or erythromycin, the plasma levels of terfenadine become sufficiently elevated to block cardiac potassium channels. Such blockage causes fatal ventricular arrhythmias.

Information from reaction phenotyping can also be used to explain or predict adverse drug reactions that result from variances in the activity of various P450 enzymes. During reaction phenotyping, the quantity and/or kind of metabolites produced when a drug reacts with an enzyme are used to identify the existence of that enzyme in an individual. The pharmacologic or toxic effects of certain drugs can be exaggerated or compounded in a significant percentage of the population-at-large due to a genetic deficiency in a P450 enzyme. The cytochrome P450 deficiencies identified to date include CYP2D6, CYP2C$_{Mp}$ and CYP2C$_{TB}$. Individuals lacking CYP2D6, CYP2C$_{Mp}$ or CYP2C$_{TB}$ were initially identified as poor metabolizers of debrisoquine, S-mephenytoin and tolbutamide, respectively. However, because each P450 enzyme has a broad substrate specificity, each genetic defect affects the metabolism of several drugs. The incidence of the poor-metabolizer phenotype varies among different ethnic groups. For example, 5–10% of Caucasians are poor metabolizers of debrisoquine, an antihypertensive drug metabolized by CYP2D6. Less than 1% of Japanese subjects are defective in CYP2D6 activity. In contrast, about 20% of Japanese subjects are poor metabolizers of S-mephenytoin, whereas less than 5% of Caucasians are so affected. Mephenytoin is an anticonvulsant metabolized by $CYP2C_{Mp}$.

Poor metabolizers often experience exaggerated responses to drugs at dosages that are well tolerated by normal subjects who have a better capability to metabolize the same drugs. If a drug is metabolized by cytochrome CYP2D6, the drug likely will have an exaggerated or toxic effect in individuals lacking CYP2D6. As noted, about 5% to 10% of all Caucasians have abnormally low concentrations of CYP2D6.

In the late 1950's, clinical trials in the United States established that sparteine was as potent as oxytocin for inducing labor at term. However, the duration and intensity of action of sparteine was dramatically increased in about 7% of all patients tested. This exaggerated response to sparteine included prolonged uterine contraction and abnormally rapid labor. In some cases, sparteine caused death of the fetus. The drug was not recommended for clinical use because these side effects were unpredictable and occurred at doses of 100–200 mg/kg, which were well tolerated by other patients. Sparteine is metabolized by CYP2D6, hence, 5–10% of all Caucasians are expected to be poor metabolizers of sparteine. This prediction is borne out by the finding that an exaggerated response to sparteine was observed in 7% of the patients administered during clinical trials.

Accordingly, it would be highly desirable to provide an apparatus and method for identifying the enzymes which metabolize a particular drug and for preventing or modifying the administration of the drug to individuals having abnormal concentrations of the enzymes which metabolize the drug.

BRIEF DESCRIPTION OF THE DRAWINGS

These and other, further and more specific objects and advantages of the invention will be apparent to those skilled in the art from the following detailed description thereof, taken in conjunction with the drawings, in which.

Figure 1:
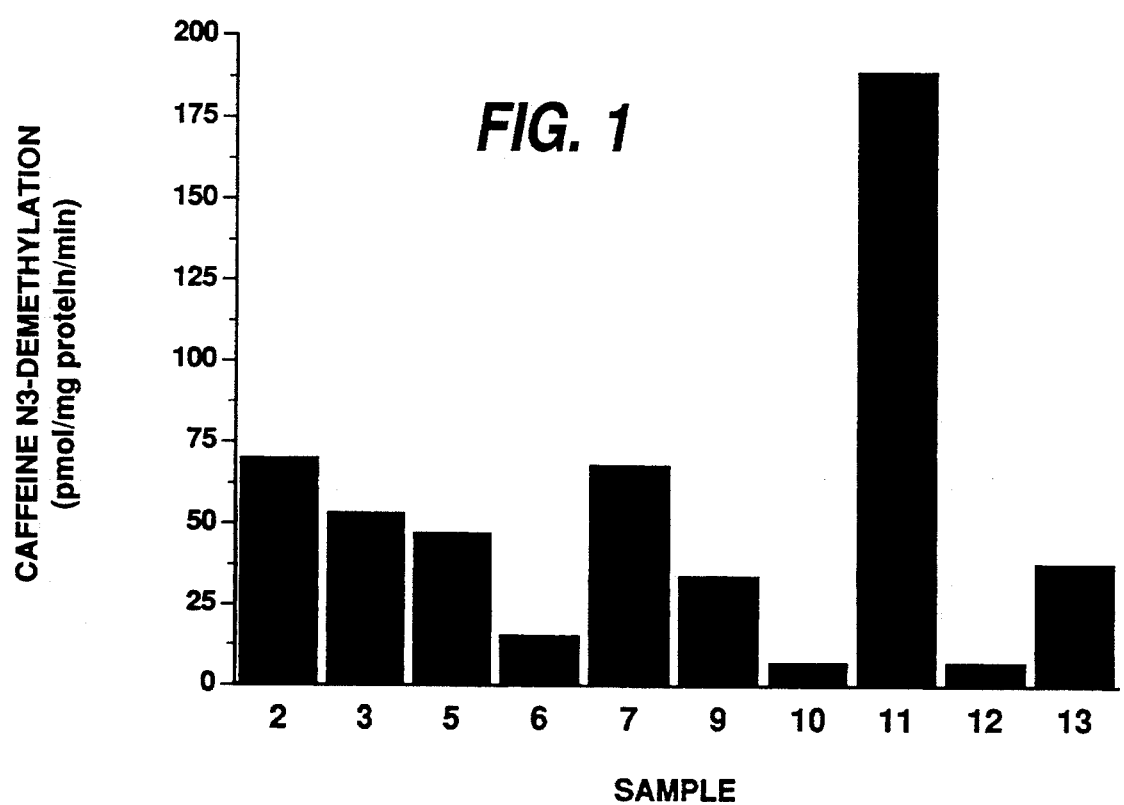
FIG. 1 is a reference graph illustrating the concentration or activity of the CYP1A2 enzyme in the livers of ten different human donors.

We have discovered a method for determining whether one of a plurality of enzymes in the human body metabolizes a drug. The method includes the step of providing for each of the enzymes a reference data tabulation indicating the activity of the enzyme in the body of each of a plurality of donors. The activity of the enzyme in one of the donors is different from the activity of the enzyme in the others of the donors. The data tabulation for each enzyme indicates the proportional relationship between the activity of the enzyme in each of the donors. The next step in the method is to provide from the body of each of said plurality of donors a donor sample of enzymes. Each donor sample is generated from the same type of body tissue and has a selected weight. The donor samples are used to generate drug metabolism data representing the rate of metabolism of the drug by each of the donor samples. The drug metabolism data is generated by contacting a fixed quantity of the drug with one of the donor samples for a selected period of time to produce a reaction mixture. The reaction mixture is analyzed to determine the quantity of metabolites present per unit weight of the donor sample. Each of the remaining donor samples is also contacted with a fixed quantity of the drug for a selected period of time to produce a reaction mixture which is analyzed to determine the quantity of metabolites present per unit weight of the donor sample. The drug metabolism data for each of the donor samples has a proportional relationship to the drug metabolism data for each of the other donor samples. The proportional relationship of drug metabolism data is compared with the proportional relationship of enzyme activity in the reference data tabulation for each of the enzymes to determine if the proportional relationship of the drug metabolism data corresponds within designated limits to the proportional relationship of enzyme activity in the reference data tabulation for one of the plurality of enzymes.

In another embodiment of the invention, we provide a kit for determining whether one of a plurality of enzymes in the human body metabolizes a drug. The kit includes a reference data tabulation for each of the enzymes. The reference data tabulation indicates the activity of the enzyme in the body of each of a plurality of donors. The activity of the enzyme in one of the donors is different from the activity of the enzyme in the other donors. The data tabulation indicates the proportional relationship between the activity of the enzyme in each of said donors. The kit also includes a plurality of donor enzyme samples. Each of the donor samples is generated from a different one of the bodies of the plurality of donors, is generated from the same type of body tissue, and has a selected weight. Each one of the donor samples is used to generate metabolism data which represents the rate of metabolism of the drug by the donor sample. The metabolism data for each donor sample is generated by contacting a fixed quantity of the drug with the donor sample for a selected period of time to produce a reaction mixture, and by analyzing the reaction mixture to determine the quantity of metabolites present per unit weight of the donor samples. The drug metabolism data for each of the donor samples has a proportional relationship to the drug metabolism data for the other donor samples. The drug metabolism data for the donor samples is collectively compared with the reference data tabulation to determine whether the metabolism data corresponds within designated limits to the proportional relationship of enzyme activity in the reference data tabulation for one of the plurality of enzymes.

By way of example, in one embodiment of our invention, the reaction phenotyping kit contains microsomes prepared from human liver samples obtained from ten different donor individuals. Each microsome is prepared solely from a liver sample obtained from one of the individuals. The preparation of microsomes from human liver is basically carried out according to published procedures. Microsomes are also known as endoplasmic reticulum, and comprise subcellular organelles containing cytochrome P450 and other enzymes that metabolize and detoxify drugs. The kit also contains samples of microsomes pooled from two or more individual samples, and contains a booklet with tabulated reference data on the variation in the activity of eight of the major P450 enzymes in the microsomes from each of the ten donor individuals. To preserve the P450 enzyme activity, the microsome samples are in capped vials and are stored frozen at −65 degrees C. to −90 degrees C and are shipped frozen on dry ice. The major P450 enzymes include the CYP1A2, CYP2A6, CYP2C$_{Mp}$, CYP2C$_{TB}$, CYP2D6, CYP2E1, CYP3A4/5 and CYP4A9/11. The activity of each of these P450 enzymes in microsomes from the ten donor individuals is determined in vitro by separately contacting a microsome from each of the ten different donor individuals with a selected reactant drug to produce a reaction mixture and by then testing the reaction mixture to determine the quantity of metabolite present. The reference data concerning the activity of the above-noted major P450 enzymes in microsomes from each of the ten donor individuals is obtained using the reactant drugs indicated below:

| Enzyme in Microsome | Reactant Drug |
| --- | --- |
| CYP1A2 | 7-Ethoxyresorufin O-dealkylation and Caffeine N3-demethylation |
| CYP2A6 | Coumarin 7-hydroxylation |
| CYP2C$_{MP}$ | S-Mephenytoin 4-hydroxylation |
| CYP2C$_{TB}$ | Tolbutamide methyl-hydroxylation |
| CYP2D6 | Dextromethorphan O-demethylation |
| CYP2E1 | Chlorzoxazone 6-hydroxylation |
| CYP3A4/5 | Testosterone 6β-hydroxylation |
| CYP4A9/11 | Lauric acid 12-hydroxylation |

Any other desired reactants can be utilized. Consequently, for example, the enzyme CYP1A2 is known to metabolize 7-ethoxyresorufin O-dealkylation and caffeine N3-demethylation (hereafter called "7-etho"). A selected fixed quantity of 7-etho is combined with a selected fixed quantity of microsome from the first donor for a selected period of time, after which the quantity of metabolites produced by interaction of the 7-etho and the enzymes in the microsome is determined. The greater the amount of metabolite, the greater the activity of the enzymes in the microsome. Since the CYP1A2 microsome is known to be primarily responsible for the metabolism of 7-etho, the quantity of metabolite produced indicates the activity of the CYP1A2 enzyme in the microsome, and, in the liver from the first donor. Reference data for each of the remaining donors is produced in the same fashion by contacting the selected fixed quantity of microsome from each donor individual with the selected fixed quantity of 7-etho for a selected period of time and then measuring the amount of metabolite produced. The resulting reference data comprises the quantity of metabolite produced by each donor's microsome. This reference data is tabulated in a reference bar graph in the booklet in the kit. Each bar in the reference bar graph indicates the quantity of metabolite produced, or, in other words, indicates the activity of the CYP1A2 enzyme in each donor's microsome. Since it is very likely that the activity of the CYP1A2 enzyme will be different for each donor, the height of each bar in the graph is different from the height of and is proportional to the other bars in the graph. Using the foregoing procedure, a separate reference bar graph is produced for each of the eight major P450 enzymes noted above. Each reference bar graph indicates the activity of one of the eight major P450 enzymes in the microsome of each of the ten donor individuals. Reference bar graphs can, of course, be produced for any number of the P450 enzymes or other enzymes. Finally, the booklet in the kit also contains a separate bar graph indicating the content in nmol/mg protein of cytochrome P450 in the microsome of each of the ten donors, contains a bar graph indicating the specific content in nmol/mg protein of NDAPH-cytochrome c reductase in the microsome of each of the ten donors, and contains another bar graph indicating the specific content in nmol/mg protein of cytochrome b5 in the microsome of each of the ten donor individuals.

In use, the reaction phenotypic kit described above is used to determine which of eight of the major P450 enzymes in the human liver is responsible for metabolizing drugs and other chemicals. Use of the kit is basically a two step process. In the first step, drug metabolism data is generated for the particular test drug being analyzed. This data is generated by combining a selected fixed quantity of the test drug with a selected fixed quantity of microsome from the first donor for a selected period of time, after which the quantity of metabolites produced by interaction of the test drug and the enzymes in the microsome is determined. The greater the amount of metabolite, the greater the activity of the enzymes in the microsome. Drug metabolism data for each of the remaining donors is produced in the same fashion by contacting a quantity of microsome from each donor with a quantity of the test drug for the same period of time as was used in obtaining data for the first donor, and by then measuring the amount of metabolite produced. The quantity of microsome and the quantity of the test drug used in generating drug metabolism data for a donor is equivalent to the quantity of microsome and test used to generate test data for each of the other donors. The resulting drug metabolism data comprises the quantity of metabolite produced by each donor's microsome on reacting with the test drug. This drug metabolism data is tabulated in bar graph form. Each bar in the graph indicates the enzyme activity in the microsome for a different one of the ten donors. Each of the ten bars in the bar graph normally is a different height than the remaining bars because the activity of the enzyme which metabolizes the test drug varies for each of the ten donors. The height of each bar in the bar graph of the drug metabolism data is proportionally related to each of the other bars. The height of the bar for the first donor may be 80% of the height of the bar for the second donor, 200% of the height of the bar for the third donor, etc. The proportional relationship of the first, second and third bars would then be 8:10:4, or 4:5:2.

The second step in the reaction phenotyping process is to compare the drug metabolism bar graph with the reference bar graph for each of the eight major P450 enzymes. If the drug metabolism bar graph closely approximates and correlates with one of the reference graphs for the eight major P450 enzymes, then it is likely that the test drug was metabolized by the P450 enzyme associated with that particular graph. Different procedures can be defined to determine if one of the reference graphs closely correlates to the drug metabolism bar graph. First, for example, a simple visual comparison can be utilized. Second, it can be required that the proportional relationship between two or more bars in the reference graph for two particular donors be equal within 5% to 10% (or within any other selected range) to the proportional relationship of two or more bars in the metabolism bar graph for the same two donors. For example, if the proportional relationship between three bars (for donors 2, 3 and 5) in a reference graph is 8.1:10:3.8 while the proportional relationship between the three bars for the same donors in the metabolism bar graph is 8:10:4, then the difference between the values for the bars for donor 2 in the two graphs is 8.0 less 8.1 which equals 0.1, which is less than a 5% difference. The difference between the values for the bars for donor 3 in the reference and metabolism graphs is 10 less 10 which equals zero, which is less than a 5% difference. The difference between the values for the bars for donor 5 in both graphs is 4.0 less 3.8 which equals 0.2, which is a difference of less than 10%. A third way to compare the data in a reference bar graph and metabolism bar graph is to compare the difference between the proportional value of two bars in the reference graph with the difference between proportional values of the two bars for the same donor in the metabolism graph. If, as noted above, the reference graph reflects a proportional relationship of 8.1:10:3.8 between the bars for donors 2, 3 and 5 while the metabolism bar graph reflects a proportional relationship of 8:10:4 between the bars for donors 2, 3, and 5 then the difference between the proportional values for donors 2 and 3 in the reference graph is 10 less 8.1 which equals a subtractant value of 1.9. The difference between the proportional values for donors 2 and 3 in the metabolism graph is 10 less 8 which equals a subtractant value of 2.0. The difference between these resulting subtractant values is 2.0 less 1.9 which equals 0.1 which is less than a 10% difference. A fourth way to compare the data embodied in a reference graph and a metabolism graph is to evaluate the data using standard statistical tests and to require in such tests that the data in the reference graph and metabolism graph correlate to one another within set limits.

The concentration, or activity, of the P450 enzymes in human liver microsomes varies enormously from person to person. The concentration of each P450 enzyme appears, however, to vary independently of the concentration of other P450 enzymes.

If the test kit of the invention had been available at the time SELDANE was developed as an anti-histamine, the role of the CYP3A enzymes in the metabolism of terfenadine could have been readily determined, and interactions with ketoconazole and erythromycin would have been predicted because ketoconazole and erythromycin have long been recognized as potent inhibitors of the CYP3A enzymes. It is anticipated that for new pharmaceuticals under development, reaction phenotyping with the apparatus of the invention will provide valuable insights into potential deleterious effects of simultaneously ingesting first and second drugs where the first drug increases or decreases the concentration of an enzyme which metabolizes the second drug or which metabolizes a metabolite of the second drug. Clinical trials can be designed to determine the effect individuals of simultaneously administering the first and second drugs. One such trial can determine the effect of simultaneously administering both drugs where the first drug increases the activity of the enzyme. Increasing the activity of the enzyme may, for example, cause a problem because the enzyme too quickly consumes the second drug. A second trial can determine the effect of simultaneously administering both drugs where the first drug decreases the activity of the enzyme. During the second trial, decreasing the activity of the enzyme may cause a problem because the second drug is not properly metabolized and is, as a result, toxic. See, for example the article "Mechanism of the Cardiotoxic Actions of Terfenadine" by Woosley, et al., JAMA, Mar. 24/31, 1993, Vol. 269 No. 12. See also "Understanding Consequences of Concurrent Therapies", Editorial, JAMA Mar. 24/31, 1993, Volume 269, No. 12; and, "Terfenadine-Ketoconazole Interaction" by Honig et al., JAMA, Mar. 24/31, Vol. 269, No. 12.

When first and second drugs are ingested by an individual and the first drug functions to alter the activity of an enzyme which metabolizes the second drug or metabolizes a metabolite of the second drug, this is called a metabolic drug-drug interaction. In a metabolic drug—drug interaction, the first and second drugs do not interact with one another, but the first drug effects the activity of enzymes which metabolize the second drug or a metabolite of the second drug. Through reaction phenotyping, it is conceivable that all drugs may one day be categorized according to which P450 enzyme is involved in their metabolism. When the need for concomitant drug therapy arises, a physician will choose drugs from different categories to reduce the possibility of a metabolic drug—drug interaction. In other words, polytherapy might be approached on a rational basis. Polytherapy means two or more drugs are concurrently administered to an individual.

Information from reaction phenotyping can also be used to explain or predict adverse drug reactions that result from genetic variances in the activity or concentration of various enzymes. For example, the development of the drug sparteine was discussed above. If the test kit and procedure of the invention had been available when sparteine was developed, the exaggerated response or toxic effect of sparteine would have been predicted to occur in 5% to 10% of Caucasians administered the drug. Further, the test kit and procedure of the invention would have suggested that possible users of sparteine be tested for deficiency of the CYP2D6 enzyme.

Apparently the only other commercially available system for reaction phenotyping involves the use of microsomes or cell lysates from human β-lymphoblastoid cells transfected with recombinant DNA (cDNA) encoding individual human P450 enzymes. This technology is available from Gentest Corporation, 6 Henshaw Street, Woburn, Ma. 01801, USA. This system can establish the ability of a P450 enzyme to catalyze a reaction, but it has several disadvantages for reaction phenotyping. First, following transfection with cDNA, the β-lymphoblastoid cells express relatively lower levels of human P450 enzymes than those present in human liver microsomes. Furthermore, the β-lymphoblastoid cells contain low levels of NADPH-cytochrome P450 reductase and cytochrome b5, which are needed to support P450 enzyme activity. Consequently, the activity of the human P450 enzymes expressed in transfected β-lymphoblastoid cells is usually considerably less than that observed with human liver microsomes. Differences in the lipid environment, differences in enzyme insertion into the endoplasmic reticulum and differences in pool translational modifications of the enzymes are additional reasons why the activity of a human P450 enzyme expressed in B-lymphoblastoid cells may differ from its activity in liver microsomes. For these and other reasons, negative results obtained with a cDNA-expressed human P450 enzyme are difficult to interpret. In other words, when a cDNA-expressed enzyme fails to metabolize a drug, it is not clear whether this reflects the inability of the enzyme to metabolize the drug or whether the enzyme could not metabolize the drug because the conditions under which the cDNA enzyme is used prevent the enzyme from metabolizing the drug.

Another apparent disadvantage with the Gentest Corporation system is that each of the human P450 enzymes is provided in about the same concentration, whereas in the method and apparatus of the invention, the concentration of the individual P450 enzymes in human liver microsome in different individuals varies enormously from one enzyme to the next. This variation is central to the effectiveness of the method of the invention. The Gentest Corporation system overestimates the activity of P450 enzymes that are present in low concentrations in human liver microsomes and underestimates the activity of P450 enzymes that are present in high concentration in human liver microsomes. A cDNA-expressed enzyme does not indicate whether that enzyme is a minor or major contributor to the metabolism of a drug in a liver.

Another drawback of the Gentest system is that the cDNA enzymes include only those human P450 enzymes what have bee cloned and expressed in β-lymphoblastoid cells. Human liver microsomes appear to contain all of the P450 enzymes which were present in the donor's liver.

The test kit and method of the invention can be used to generate in vitro metabolites that would likely be formed in a human. Identifying the metabolites produced by the interaction of an enzyme an a drug can be important. Sometimes, for example, the pharmacological effects of a drug are due to a metabolite of the drug and not to the drug in its original ingested form. Or, the metabolite may be toxic, in which case the drug may be altered to block formation of toxic metabolites.

The test kit and method of the invention can be utilized in conjunction with enzymes other than P450 enzymes. For example, liver microsomes contain other drug-metabolizing enzymes such as UDP-glucuronosyltransferases, carboxylesterases, epoxide hydrolases, flavin-containing monooxygenases, and N-acetyltransferases. Other drug-metabolizing enzymes are located in liver cytosol or mitochondria, namely sulfotransferases, glutathione S-transferases, carboxylesterases, epoxide hydrolases, N-acetyltransferases, methyltransferases, carbonyl reductases, monoamine and diamine oxidases and others.

P450 enzymes in frozen liver microsomes appear to be relatively stable. Storing human liver at −65 degrees C. to −90 degrees C for up to six months produces no detectable degradation of CYP1A2, CYP2A6, $CYP2C_{Mp}$, $CYP2C_{TB}$, CYP2D6, CYP2E1, CYP3A4/5 and CYP4A9/11. Partial loss of enzyme activity does not limit the usefulness of the test kit of the invention because the loss of enzyme activity is ordinarily uniform among all microsomes in the test kit.

Once the method and kit of the invention have identified an enzyme which is responsible for metabolizing a particular drug, this finding can be further confirmed by applying a chemical or antibody inhibitor to a microsome in the kit. The inhibitor attaches to the binding site of the enzyme and tends to prevent the enzyme from metabolizing a particular drug. The microsome, thus treated, is then contacted by the drug for a selected period of time. If metabolites are not produced, or are produced in a significantly reduced concentration, then the ability of the enzyme to metabolize the drug is further confirmed. If there is cause to believe two or more enzymes are responsible for the metabolism of a drug, these enzymes can be individually or simultaneously disabled when additional tests are carried out in which the drug being tested in contacted with a microsome from a donor.

The Ames assay is a test to determine whether a chemical may function as a mutagen and eventually alter the DNA of human cells and/or whether a chemical produces metabolites which may function as a mutagen and eventually alter the DNA of human cells. The Ames assay utilizes microsomes prepared from the livers of rats treated with Aroclor 1254. The Aroclor 1254 significantly increases the enzyme concentration in the livers. The rat microsomes are intermixed in a buffer solution with the chemical being tested and with a selected bacteria to form a reactant solution. The bacteria is of a type which can be easily examined to determine if cross linkage in the bacteria DNA occurs. The rat microsome, because of the high concentration of enzymes in the microsome, produces a large quantity of metabolites in the reactant solution. After the reactant solution is allowed to set for a selected period of time, bacteria are removed and examined to determine whether DNA in the bacteria have cross linked. The drawback to this procedure is that rats have enzymes not found in humans and vice-versa. According to one embodiment of the invention and as an alternate to the Ames assay, microsome buffer samples from a plurality of donors are intermixed to form a pooled microsome buffer sample which likely contains significant levels of all enzymes found in the human liver. This pooled microsome buffer sample is then intermixed with a supplemental buffer solution, with the chemical being tested, and with bacteria for a selected period of time, after which the bacteria are examined to determine if cross linkage of the DNA in the bacteria has occurred. This procedure is believed to be much more reliable than the Ames assay because it insures that all human liver enzymes are present. The human enzyme "soup" can sometimes produce a much different metabolite mix than the rat enzyme "soup". Further, to insure that the chemical being tested is contacted with as many human enzymes as possible, the chemical can, instead of the microsomes, be contacted with a composition comprising pooled S9 fractions each obtained from one of a plurality of human donors.

The following examples are presented, not by way of limitation of the scope of the invention, but to illustrate to those skilled in the art the practice of various of the presently preferred embodiments of the invention and to distinguish the invention from the prior art.

EXAMPLE 1

Frozen livers were obtained from each of the deceased donors noted below in TABLE I.

TABLE I

| | Donor Information | | | | |
|---|---|---|---|---|---|
| Donor | Gender | Age (yrs) | Race | Smoker | Alcohol Use |
| 2 | F | 53 | Caucasian | Yes | No |
| 3 | M | 33 | Caucasian | Yes | Yes |
| 5 | M | 42 | Caucasian | No | No |
| 6 | F | 51 | Caucasian | Yes | Yes |
| 7 | M | 45 | Caucasian | Yes | Yes |
| 9 | F | 11 months | Caucasian | No | No |
| 10 | F | 54 | Hispanic | No | Yes |
| 11 | M | 54 | African-American | No | Yes |
| 12 | F | 36 | Caucasian | ? | Yes |
| 13 | F | 52 | Caucasian | Yes | Yes |

Serology tests were performed on each donor for HIV, HTLV-I, RPR, CMV, HBsAg, and HCV. These tests were all negative except that the CMV test was Pos/Neg for donor 2, and the CMV test was Positive for donors 6, 10, 11, and 12. Each frozen liver was processed as follows to produce microsome sample buffer solution. The liver was dissected into small sections which were added to and homogenized in a chilled buffer solution having a neutral pH. The homogenate was centrifuged at 9,000 x g to remove the larger cellular particles in the form of a primary pellet which was discarded. The resulting liquid supernant, called the S9 fraction, contained microsomes and other enzymes. The S9 fraction was centrifuged at 100,000 x g to produce a secondary pellet of microsomes. The remaining liquid was discarded. The secondary pellet was reconstituted in a buffered wash solution which was centrifuged at about 100,000 x g to recapture the secondary pellet. The wash solution was discarded. The secondary microsome pellet was reconstituted in a sucrose buffer solution at a concentration of 20 mg of protein per ml of sucrose buffer solution to form a microsome sample solution. The microsome sample solution was frozen.

EXAMPLE 2

Equal amounts of each of five of the microsome sample solutions of Example 1 are intermixed to form a pooled microsome sample solutions. The pooled microsome sample solution is intermixed in a supplemental buffer solution with a test drug and NADPH for a selected period of time. The solution is analyzed to identify the kind and concentration of metabolites present.

EXAMPLE 3

Example 2 is repeated a plurality of times, varying the pH of the buffer solution, the concentration of the test drug, the concentration of enzymes, and other factors to determine the optimal assay conditions. The optimal assay conditions are the conditions under which a test drug best reacts with an enzyme or enzymes in the microsome.

EXAMPLE 4

Examples 2 and 3 were repeated utilizing caffeine as the test drug. The optimal assay conditions for caffeine were determined.

The reference data graph of FIG. 1 was generated by forming reactant solutions by, for each donor in Example 1, intermixing in a buffer solution with caffeine and NADPH at a selected desirable temperature a selected fixed amount, for example 1 ml, of the frozen microsome sample buffer solution derived from the donor's liver. A selected fixed amount, for example one milligram, of the caffeine was utilized. The NADPH functioned as an oxidation-reduction generation system. The quantities of microsome sample solution, supplemental buffer solution, NADPH, and caffeine utilized can vary as desired but are ordinarily selected in accordance with the optimal assay conditions. The NADPH facilitates the interaction of the enzymes in the sample buffer solution with the caffeine to produce metabolites. It is known that caffeine is metabolized by the CYP1A2 enzyme. After a selected period of time, the reaction between the CYP1A2 enzyme and the caffeine was halted. The quantity of metabolites produced by the interaction of the CYP1A2 enzyme and caffeine was determined. Spectrography and other analytical procedures for quantifying and identifying metabolites produced by interaction of a drug with enzymes are well known in the art and are not discussed herein. Consequently, as noted above in this Example 2, buffer sample solution from donor 2 was interacted with caffeine in a reactant solution including NADPH and supplemental buffer solution and the quantity of metabolite determined; buffer sample solution from donor 3 was interacted with caffeine in a reactant solution including NADPH and supplemental buffer solution and the quantity of metabolite determined; and so on for each donor. The quantity of metabolite in pmol/mg protein/min produced by the microsome of each donor is tabulated in the graph of FIG. 1 and indicates the activity of the CYP1A2 enzyme in each donor.

EXAMPLE 5

Examples 2 and 3 were repeated utilizing coumarin as the test drug. The optimal assay conditions for coumarin were determined.

Figure 2:
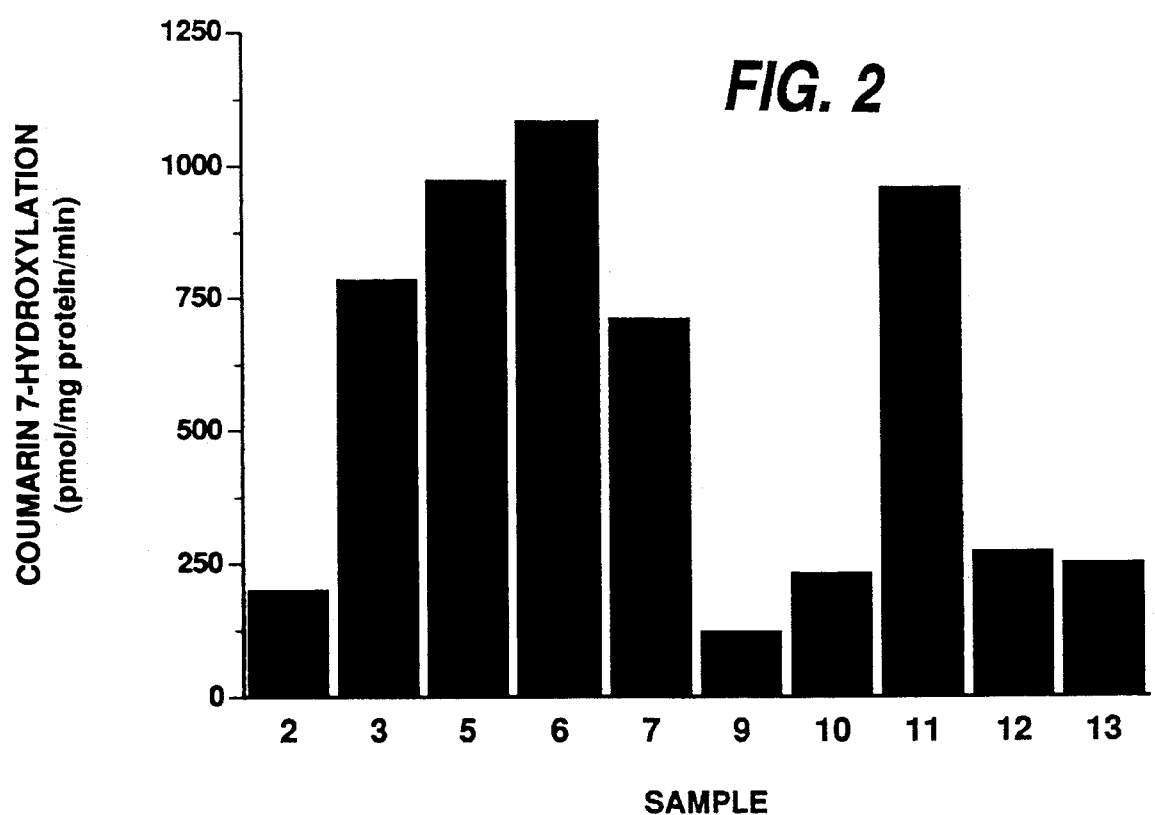
FIG. 2 is a reference graph illustrating the concentration or activity of the CYP2A6 enzyme in the livers of the ten human donors used to generate the data for the graph of FIG. 1.

The reference data graph of FIG. 2 was generated by forming reactant solutions by, for each donor in Example 1, intermixing in a buffer solution with coumarin and NADPH at a selected desired temperature a selected fixed amount, for example 1 ml, of the frozen microsome sample buffer solution derived from the donor's liver. A selected fixed amount, for example one milligram, of the coumarin was utilized. The NADPH functioned as an oxidation-reduction generation system. The quantities of microsome buffer solution, supplemental buffer solution, NADPH, and coumarin used can vary as desired but are ordinarily selected in accordance with the optimal assay conditions. The NADPH facilitated the interaction of the enzymes in the sample buffer solution with the coumarin to produce metabolites. It is known that coumarin is metabolized by the CYP2A6 enzyme. After the enzymes and coumarin reacted for a selected period of time, the reaction was halted. The quantity of metabolites produced by the interaction of the CYP2A6 enzyme and coumarin was determined. Spectrography and other analytical procedures for quantifying and identifying metabolites produced by interaction of a drug with enzymes are well known in the art and are not discussed herein. Consequently, as noted above in this Example 3, buffer sample solution from donor 2 was interacted with coumarin in a reactant solution including NADPH and supplemental buffer solution and the quantity of metabolite determined; buffer sample solution from donor 3 was interacted with coumarin in a reactant solution including NADPH and supplemental buffer solution and the quantity of metabolite determined; and so on for each donor. The quantity of metabolite in pmol/mg protein/min produced by the microsome of each donor is tabulated in the graph of FIG. 2 and indicates the activity of the CYP2A6 enzyme in each donor.

EXAMPLE 6

Examples 2 and 3 were repeated utilizing dextromethophan as the test drug. The optimal assay conditions for dextromethophan were determined.

Figure 3:
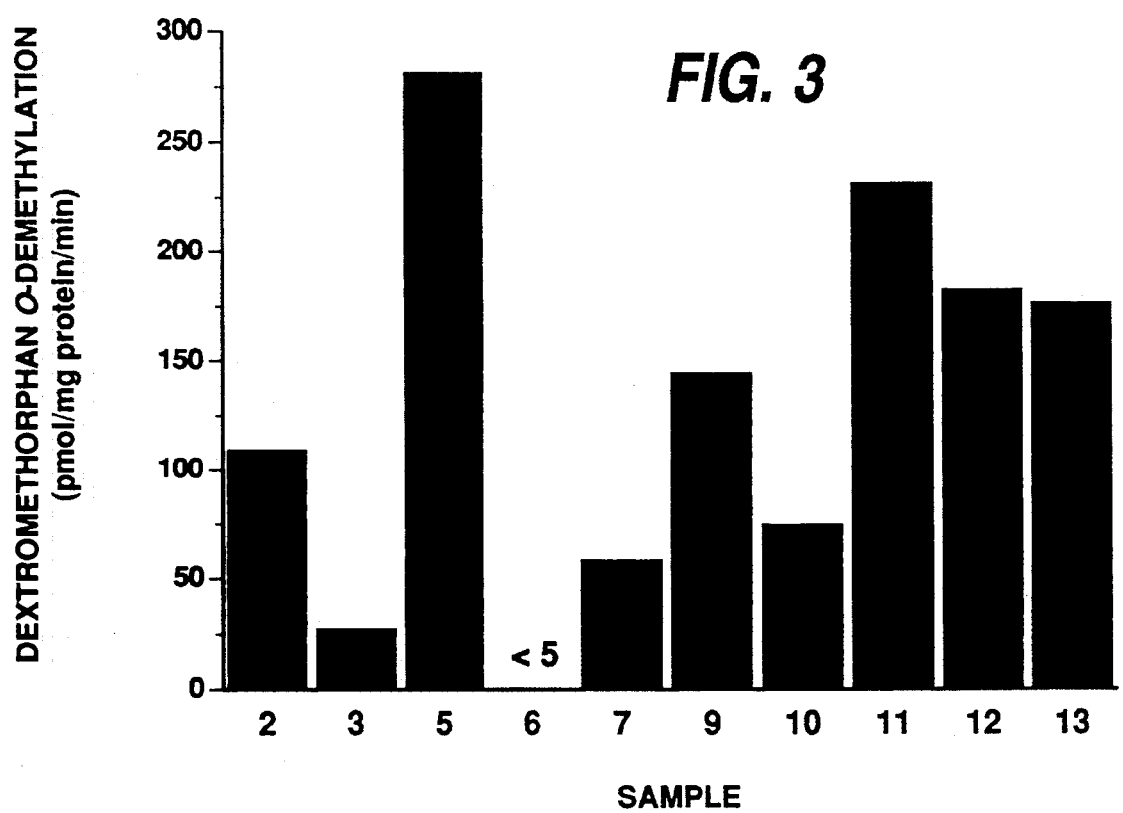
FIG. 3 is a reference graph illustrating the concentration of activity of the CYP2D6 enzyme in the livers of the ten human donors used to generate the data for the graph of FIG. 1; and, FIG. 4 is a graph illustrating the quantity of metabolites produced by a drug when the drug is contacted with microsomes from the livers of each of the ten different human donors utilized to generate the graphical reference data of FIGS. 1 to 3.

The reference data graph of FIG. 3 was generated by forming reactant solutions by, for each donor in Example 1, intermixing in a buffer solution with dextromethophan and NADPH at a selected desirable temperature a selected fixed amount, for example 1 ml, of the frozen microsome sample buffer solution derived from the donor's liver. A selected fixed amount, for example one milligram, of the dextromethophan was utilized. The NADPH functioned as an oxidation-reduction generation system. The quantities of microsome sample solution, supplemental buffer solution, NADPH, and dextromethorphan can vary as desired, but ordinarily are selected in accordance with optimal assay conditions. The NADPH facilitated the interaction of the enzymes in the sample buffer solution with the dextromethorphan to produce metabolites. It is known that dextromethorphan is metabolized by the CYP2D6 enzyme. After a selected period of time, the reaction between the CYP2D6 enzyme and dextromethorphan was halted. The quantity of metabolites produced by the interaction of the CYP2D6 enzyme and dextromethorphan in the reactant solution was determined. Spectrography and other analytical procedures for quantifying and identifying metabolites produced by interaction of a drug with enzymes are well known in the art and are not discussed herein. Consequently, as noted above in this Example 4, buffer sample solution from donor 2 was interacted with dextromethorphan in a reactant solution including supplemental buffer solution and NADPH and the quantity of metabolite determined; buffer sample solution from donor 3 was interacted with dextromethorphan in a reactant solution including supplemental buffer solution and NADPH and the quantity of metabolite determined; and so on for each donor. The quantity of metabolite in pmol/mg protein/min produced by the microsome of each donor is tabulated in the graph of FIG. 3 and indicates the activity of the CYP2D6 enzyme in each donor.

EXAMPLE 7

Examples 2 and 3 are repeated utilizing sparteine as the test drug. The optimal assay conditions for sparteine were determined.

Figure 4:
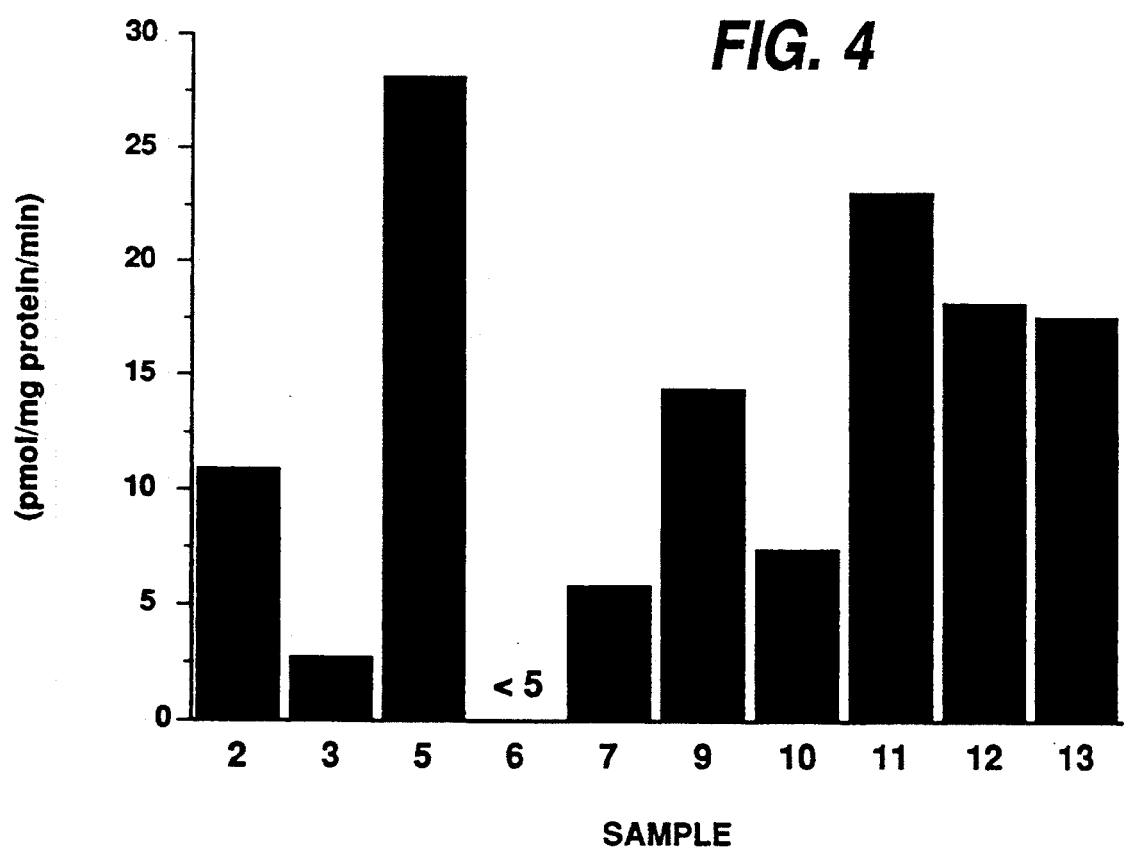

The drug metabolism data graph of FIG. 4 is generated by forming reactant solutions by, for each donor in Example 1, intermixing in a buffer solution with a test drug and NADPH at a selected desired temperature a selected fixed amount, for example 1 ml, of the frozen microsome sample buffer solution derived from the donor's liver. A selected fixed amount, for example one milliliter, of the test drug is utilized. The NADPH functioned as an oxidation-reduction generation system. The quantities of the microsome sample solution, supplemental buffer solution, NADPH, and test drug can vary as desired, but ordinarily are varied in accordance with optimal assay conditions. The test drug is sparteine. The NADPH facilitates the interaction of the enzymes in the sample buffer solution with the sparteine to produce metabolites. The quantity of metabolites produced by the interaction of the enzyme(s) and sparteine in the reactant solution is determined. Spectrography and other analytical procedures for quantifying and identifying metabolites produced by interaction of a drug with enzymes are well known in the art and are not discussed herein. Consequently, as noted above in this Example 5, buffer sample solution from donor 2 is interacted with sparteine in a reactant solution including supplemental buffer solution and NADPH and the quantity of metabolite determined; buffer sample solution from donor 3 is interacted with sparteine in a reactant solution including supplemental buffer solution and NADPH and the quantity of metabolite determined; and so on for each donor. The quantity of metabolite in pmol/mg protein/min produced by the microsome of each donor, i.e. the drug metabolism data, is tabulated in the graph of FIG. 4 and indicates the metabolic enzyme activity of each donor. The graph of FIG. 4 is compared with the graphs of FIGS. 1 to 3. Since the graph of FIG. 4 is very similar to the graph of FIG. 3, it appears very likely that sparteine is metabolized by the CYP2D6 enzyme.

EXAMPLE 8

Examples 2 and 3 are repeated utilizing sparteine as the test drug. The optimal assay conditions for sparteine were determined.

A reactant solution is formed by mixing at a selected desirable temperature a selected fixed amount, for example one ml, of the frozen microsome sample buffer solution of donor 2 in a supplemental buffer solution along with an antibody which attaches to the CYP2D6 enzyme and prevents it from metabolizing drugs. After a selected period of time, NADPH and a selected amount of sparteine, for example one milligram, are mixed into the reactant solution. The quantities of microsome buffer solution, supplemental buffer solution, NADPH, and sparteine can vary as desired, but ordinarily are selected in accordance with optimal assay conditions. After a selected period of time passes, the sparteine—enzyme reaction is halted. The quantity of metabolites produced by the interaction of the enzyme(s) and sparteine in the reactant solution is determined. The quantity of metabolites is very small, confirming that the CYP2D6 enzyme is the primary enzyme which metabolizes sparteine. The foregoing procedure in this Example 6 is repeated nine times. Each time the procedure is repeated, a sample microsome solution from a different one of the remaining donors is utilized. Similar results are obtained in that during each of the nine repetitions of the procedure the quantity of metabolite is very small, confirming that when the CYP2D6 enzyme is disabled, the sparteine is not metabolized.

EXAMPLE 9

A reactant solution is formed by mixing at a selected desired temperature a selected fixed amount, for example 1 ml, of the frozen microsome sample buffer solution of donor 2 in a supplemental buffer solution along with an antibody which attaches to CYP3A4 enzyme and prevents it from metabolizing drugs. After a selected desirable period of time, NADPH and a selected amount, for example one milligram, of a drug metabolized by CYP3A4 are mixed into the reactant solution. The amounts of microsome buffer solution, supplemental buffer solution, NADPH and antibody can vary as desired, but ordinarily are selected in accordance with optimal assay conditions. After a selected period of time passes, the drug-enzyme reaction is halted. The quantity of metabolites produced by the interaction of the enzyme(s) and drug in the reactant solution is determined. Metabolites are identified in the reactant solution. The metabolites are different from the metabolites produced by the interaction of CYP3A4 and the drug. The foregoing procedure in this Example 7 is repeated nine times. Each time the procedure is repeated, a sample microsome solution from a different one of the remaining donors is utilized. Similar results are obtained in that during each of the nine repetitions of the procedure metabolite is produced which is different from the metabolite produced when the drug is metabolized by CYP3A4. Consequently, the nine repetitions of the procedure confirm that when the CYP3A4 enzyme is disabled, another enzyme metabolizes the drug.

EXAMPLE 10

Equal amounts of each of five of the microsome sample solutions of Example 1 are intermixed to form a pooled microsome sample solutions. The pooled microsome sample solution is intermixed in a supplemental buffer solution with a test drug and NADPH for a selected period of time under optimal assay conditions. The solution is analyzed to identify the kind and concentration of metabolites present.

Having described the invention in such terms as to enable those skilled in the art to understand and practice it, and having described the presently preferred embodiments thereof, we claim:

1. A method for determining whether an enzyme in the human body metabolizes a drug, comprising the steps of
   (a) providing for the enzyme a reference data tabulation quantifying the activity of the enzyme in the body of each of a plurality of donors, the activity of the enzyme in one of said donors being different from the activity of the enzyme in each of the other of said donors, the activity of the enzyme in said one of said donors with respect to the activity of the enzyme in each of the other of said donors defining a first proportional relationship;
   (b) providing from the body of each of said plurality of donors a donor sample of enzymes, each of said donor samples
      (i) being generated from the same type of body tissue, and
      (ii) having a known weight of the enzyme;
   (c) generating drug metabolism data representing the rate of metabolism of the drug by one of said donor samples, said drug metabolism data being generated by
      (i) contacting a fixed quantity of said drug with said one of said donor samples for a selected period of time to produce a reaction mixture;
      (ii) analyzing said reaction mixture to determine the quantity of metabolites present per unit weight of the enzyme in said one of said donor samples;
   (d) repeating step (c) for each of the remaining ones of said donor samples, said quantity of metabolites present in said reaction mixture for said one of said donor samples with respect to the quantity of metabolites present in said reaction mixture for each of the other of said donor samples defining a second proportional relationship;
   (e) comparing said second proportional relationship to said first proportional relationship to determine if said second proportional relationship corresponds within designated limits to said first proportional relationship.

2. The method of claim 1 wherein the enzyme is a liver enzyme.

* * * * *